United States Patent [19]

Sugiyama et al.

[11] Patent Number: 5,376,643
[45] Date of Patent: Dec. 27, 1994

[54] COMPOSITION FOR APPLICATION TO HAIR

[75] Inventors: Keikichi Sugiyama, Kanagawa; Koji Takada, Fujisawa; Ikuo Yamamoto, Odawara, all of Japan

[73] Assignee: Lion Corporation, Tokyo, Japan

[21] Appl. No.: 684,461

[22] Filed: Sep. 20, 1990

Related U.S. Application Data

[63] Continuation of Ser. No. 304,584, Feb. 1, 1989, abandoned, which is a continuation-in-part of Ser. No. 97,621, Sep. 16, 1987, abandoned.

[30] Foreign Application Priority Data

Sep. 18, 1986 [JP] Japan ................... 61-220211
Apr. 28, 1987 [JP] Japan ................... 62-105230

[51] Int. Cl.$^5$ ........................... A61K 31/52
[52] U.S. Cl. ........................... 514/47; 514/880; 424/70.6
[58] Field of Search ............... 514/47, 48, 880; 424/70

[56] References Cited

U.S. PATENT DOCUMENTS

| | | | |
|---|---|---|---|
| 3,849,553 | 11/1974 | Dea et al. | 514/47 |
| 3,978,213 | 8/1976 | Lapinet et al. | 514/47 |
| 4,048,307 | 9/1977 | Yokota et al. | 514/47 |
| 4,208,406 | 6/1980 | Lapinet et al. | 514/47 |
| 4,211,770 | 7/1980 | Voorhees | 514/47 |
| 4,369,181 | 1/1983 | Miller et al. | 514/48 |
| 4,478,853 | 10/1984 | Chaussee | 424/70 |
| 4,745,103 | 5/1988 | Oono et al. | 514/23 |
| 5,318,776 | 6/1994 | Sugiyama et al. | 424/70 |

FOREIGN PATENT DOCUMENTS

| | | | |
|---|---|---|---|
| 2139183 | 7/1971 | Germany | 424/70 |
| 0075339 | 7/1978 | Japan | 424/70 |
| 0179110 | 11/1982 | Japan | 424/70 |
| 0230100 | 12/1984 | Japan | 424/70 |
| 1007205 | 1/1986 | Japan | 424/70 |

OTHER PUBLICATIONS

Thomas, Chem. Abstr. 67:36348s (1967).
Janistyn, Chem Abstr 78:283596 (1973).
Oshima, Chem. Abstr. 103:109,758z (1985).
Weatherhead et al., Chem. Abstr. 95:162,387z (1981).
Igarashi et al., Chem. Abstr. 106:182695t (1985).
Journal of Endocr., vol. 90, pp. 89–96 (1981).
European Search Report/Official Action, Jan. 16, 1992, K. Douschan.

*Primary Examiner*—John W. Rollins
*Assistant Examiner*—James O. Wilson
*Attorney, Agent, or Firm*—Burns, Doane, Swecker & Mathis

[57] ABSTRACT

Methods and compositions for restoring grayed hair to its natural color comprising at least one compound of the formula:

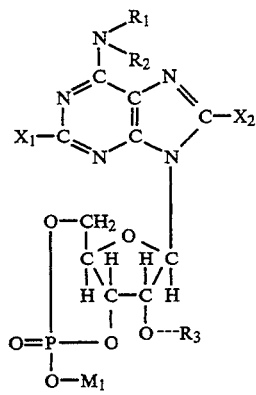

wherein $R_1$, $R_2$ and $R_3$ may be the same or different and each represents a hydrogen atom, an acyl group having 5 to 15 carbon atoms derived from a monocarboxylic acid having 5 to 15 carbon atoms or an acyl group having 2 to 15 carbon atoms derived from a dicarboxylic acid having 2 to 15 carbon atoms or an alkyl group having 1 to 2 carbon atoms; $X_1$ and $X_2$, respectively, represent a hydrogen atom, a halogen, or a mercapto group; with the proviso that when $R_1$, $R_2$ and $R_3$ and $X_1$ are hydrogen atoms at the same time, $X_2$ is not a halogen atom or a mercapto group, and $M_1$ represents a hydrogen atom, an alkali metal or tris(hydroxymethyl)aminomethane.

7 Claims, No Drawings

COMPOSITION FOR APPLICATION TO HAIR

CROSS-REFERENCE TO RELATED APPLICATION

This application is a continuation of application Ser. No. 07/304,584, filed Feb. 1, 1989, which is a CIP application of application Ser. No. 07/097,621, filed Sep. 16, 1987, both abandoned.

BACKGROUND OF THE INVENTION

Field of the Invention

The present invention relates to a composition for application to hair in the manner of a hair tonic, which, upon application to the scalp, activates melanocytes of the radix pili and improves synthesis of melanin, thereby preventing graying of the hair and restoring grayed hair to its natural color.

Graying of the hair is a universal aging phenomena, while hair dyes are commonly used to dye grayed hair, the use of such dyes is troublesome and sometimes causes side-effects such as rash. Therefore, many users find hair dyes to be an unsatisfactory solution. There has thus been a great need for developing a pharmaceutical agent or a cosmetic composition for hair capable of essentially preventing graying of the hair and restoring grayed hair to its natural color.

Heretofore, there have been developed various kinds of drugs for activating the radix pili and promoting the growth of hair. On the other hand, there have been reported only a few cosmetic compositions for preventing graying of the hair and restoring grayed hair to its natural color (see, for instance, Japanese Patent Un-examined Publication (KOKAI) Nos. 60-174705, 61-165310, 62-45527, 62-63509 and 62-63510). Moreover, the reported techniques suffer from various disadvantages such as low effectiveness, low stability of the active components and insufficient safety.

The composition disclosed in Japanese Patent Unexamined Publication No. 60-174705 employs vitamin $D_3$ and derivatives thereof. However, the cosmetic agent is incomplete in the following points:

(i) It is difficult to form the vitamin $D_3$ and its derivatives into cosmetic preparations since they are extremely unstable in the air and easily undergo oxidation, so that the cosmetic agent cannot be expected to provide sufficient effect when applied as external preparation;

(ii) Vitamin $D_3$ and the derivatives thereof tend to cause side-effects such as hypervitaminosis D or hypercalcemia (anorexia, vomiting, constipation, disponderal, degrowth and the like) and, therefore, there has been some doubt about safety.

Consequently, the cosmetic compositions disclosed in the above-mentioned Un-examined Publications are of little practical use.

SUMMARY OF THE INVENTION

Many people are annoyed by their grayed hair and there is a great need for developing compositions for preventing graying of the hair or restoring grayed hair to its natural color without causing side-effects such as those mentioned above.

Accordingly, it is a principal object of the present invention to provide a composition for application to hair which is capable of preventing graying of the hair or restoring grayed hair to its natural color upon application of the same to the scalp and which causes no side-effects and has high safety.

The present invention has been completed on the basis of the discovery that the aforementioned problems can effectively be eliminated by using a specific nucleic acid related material and derivatives thereof, which are present in various tissues and cells of the living organisms in trace amounts, and have various regulatory and physiological effects; or in combination with a specific substance having an odd number of carbon atoms, which is known to have excellent hair growth promoting effect as an effective component of hair growth agents (see Japanese Patent Un-examined Publication Nos. 59-27809 and 60-4113).

According to the present invention, the foregoing and other objects can be effectively accomplished by providing a composition for application to hair (or the scalp) which comprises (i) at least one component (A) (nucleic acid related substance) selected from the group consisting of compounds having the following general formula (I), flavin adenine dinucleotide and salts thereof:

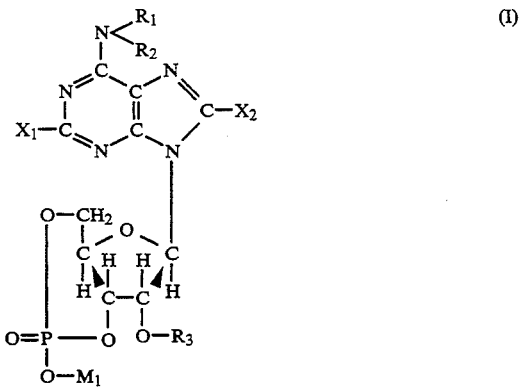

and (ii) an inert carrier. In the general formula (I), $R_1$, $R_2$ and $R_3$ may be the same or different and each represents hydrogen atom, an acyl group having 1 to 25, preferably 1 to 19 carbon atoms or an alkyl group having 1 to 25, preferably 1 to 19 carbon atoms; $X_1$ and $X_2$, respectively, represent hydrogen atom; a halogen atom such as fluorine, chlorine, bromine or iodine; a sulfur-containing group such as mercapto group, a thioalkyl group having 1 to 4 carbon atoms, 4-chlorophenylthio group and thiobenzyl group; amino group; an aminoalkyl group having 1 to 4 carbon atoms; or hydroxyl group; and $M_1$ represents hydrogen atom or a salt-forming cation such as an alkali metal (e.g., sodium, potassium or lithium) and tris(hydroxymethyl)aminomethane. In this respect, the acyl and alkyl groups may each have a substituent such as a halogen atom and may further include an aromatic ring. Moreover, the acyl group may be one derived from a dibasic acid.

According to another aspect of the present invention, a composition which comprises, as another essential component, component (B) selected from the group consisting of fatty acids, alcohols and derivatives thereof having an odd number of carbon atoms other than the foregoing component (A) is also provided.

DESCRIPTION OF THE PREFERRED EMBODIMENTS

Examples of the compounds represented by the general formula (I) include adenosine 3',5'-cyclic phosphoric acid (compound of the formula (I) in which all of $R_1$, $R_2$, $R_3$, $X_1$, $X_2$ and $M_1$ are hydrogen atoms; hereunder referred to as cAMP), the specific derivatives and the salts thereof.

These compounds, flavin adenine dinucleotide (hereunder referred to as FAD) and the salts thereof will hereinafter be explained in more detail.

(a) Compounds Represented by the General Formula (I):

cAMP as used herein is a physiologically important material which exerts regulatory function on various effects of hormones in the living organisms and it has practically been used as a biochemical reagent and medicine effective for cardiac diseases. cAMP has been produced using fermentation techniques and synthetic methods on an industrial scale. Moreover, a variety of derivatives thereof which are improved in cell membrane permeability or in stability within the living organisms are commercially available.

Specific examples of compounds (I) include those listed in the following Table I and sodium, potassium and lithium salts thereof which may be incorporated into the composition of the present invention alone or in combination. In Table I and hereinafter, the abbreviation ClPhS denotes 4-chlorophenylthio group.

TABLE I

| Groups | $R_1$ | $R_2$ | $R_3$ | $X_1$ | $X_2$ |
|---|---|---|---|---|---|
| 1(cAMP) | H | H | H | H | H |
| 2 | acetyl | H | H | H | H |
|  | butyryl | H | H | H | H |
|  | hexanoyl | H | H | H | H |
|  | octanoyl | H | H | H | H |
|  | lauroyl | H | H | H | H |
|  | pentadecanoyl | H | H | H | H |
|  | malonyl | H | H | H | H |
|  | succinyl | H | H | H | H |
|  | benzoyl | H | H | H | H |
|  | methyl | H | H | H | H |
|  | ethyl | H | H | H | H |
|  | ethyl | ethyl | H | H | H |
| 3 | acetyl | H | H | amino | H |
|  | acetyl | H | H | aminomethyl | H |
|  | butyryl | H | H | Br | H |
|  | butyryl | H | H | ClPhS | H |
|  | succinyl | H | H | Br | H |
|  | succinyl | H | H | ClPhS | H |
|  | ethyl | H | H | Cl | H |
|  | ethyl | H | H | mercapto | H |
| 4 | acetyl | H | H | H | amino |
|  | acetyl | H | H | H | aminomethyl |
|  | butyryl | H | H | H | Br |
|  | butyryl | H | H | H | ClPhS |
|  | succinyl | H | H | H | Br |
|  | succinyl | H | H | H | ClPhS |
|  | ethyl | H | H | H | Cl |
|  | ethyl | H | H | H | mercapto |
| 5 | H | H | acetyl | H | H |
|  | H | H | butyryl | H | H |
|  | H | H | hexanoyl | H | H |
|  | H | H | octanoyl | H | H |
|  | H | H | lauroyl | H | H |
|  | H | H | pentadecanoyl | H | H |
|  | H | H | malonyl | H | H |
|  | H | H | succinyl | H | H |
|  | H | H | benzcyl | H | H |
|  | H | H | methyl | H | H |
|  | H | H | ethyl | H | H |
| 6 | H | H | acetyl | amino | H |
|  | H | H | acetyl | aminomethyl | H |
|  | H | H | butyryl | Br | H |
|  | H | ·H | butyryl | ClPhS | H |
|  | H | H | succinyl | Br | H |
|  | H | H | succinyl | ClPhS | H |
|  | H | H | ethyl | Cl | H |
|  | H | H | ethyl | mercapto | H |
| 7 | H | H | acetyl | H | amino |
|  | H | H | acetyl | H | aminomethyl |
|  | H | H | butyryl | H | Br |
|  | H | H | butryl | H | ClPhS |
|  | H | H | succinyl | H | Br |
|  | H | H | succinyl | H | ClPhS |
|  | H | H | ethyl | H | Cl |
|  | H | H | ethyl | H | mercapto |
| 8 | H | H | H | Br | H |
|  | H | H | H | Cl | H |
|  | H | H | H | mercapto | H |
|  | H | H | H | thiomethyl | H |
|  | H | H | H | ClPhS | H |
|  | H | H | H | amino | H |
|  | H | H | H | aminomethyl | H |
|  | H | H | H | hydroxyl | H |
| 9 | H | H | H | H | Br |

TABLE I-continued

| Groups | $R_1$ | $R_2$ | $R_3$ | $X_1$ | $X_2$ |
|---|---|---|---|---|---|
| | H | H | H | H | Cl |
| | H | H | H | H | mercapto |
| | H | H | H | H | thiomethyl |
| | H | H | H | H | ClPhS |
| | H | H | H | H | amino |
| | H | H | H | H | aminomethyl |
| | H | H | H | H | hydroxyl |
| 10 | H | H | H | Br | Br |
| | H | H | H | Cl | Cl |
| | H | H | H | mercapto | mercapto |
| | H | H | H | thiomethyl | thiomethyl |
| | H | H | H | ClPhS | ClPhS |
| | H | H | H | amino | amino |
| | H | H | H | aminomethyl | aminomethyl |
| | H | H | H | hydroxyl | hydroxyl |
| 11 | acetyl | H | acetyl | H | H |
| | butyryl | H | butyryl | H | H |
| | hexanoyl | H | hexanoyl | H | H |
| | octanoyl | H | octanoyl | H | H |
| | lauroyl | H | lauroyl | H | ii |
| | pentadecanoyl | H | pentadecanoyl | H | H |
| | malonyl | H | malonyl | H | H |
| | succinyl | H | succinyl | H | H |
| | benzoyl | H | benzoyl | H | H |
| | methyl | H | methyl | H | H |
| | ethyl | H | ethyl | H | H |
| 12 | acetyl | H | acetyl | amino | H |
| | acetyl | H | acetyl | aminomethyl | H |
| | butyryl | H | butyryl | Br | H |
| | butyryl | H | butyryl | ClPhS | H |
| | succinyl | H | succinyl | Br | H |
| | succinyl | H | suceinyl | ClPhS | H |
| | ethyl | H | ethyl | Cl | H |
| | ethyl | H | ethyl | mercapto | H |
| 13 | acetyl | H | acetyl | H | amino |
| | acetyl | H | acetyl | H | aminomethyl |
| | butyryl | H | butyryl | H | Br |
| | butyryl | H | butyryl | H | ClPhS |
| | succinyl | H | succinyl | H | Br |
| | succinyl | H | succinyl | H | ClPhS |
| | ethyl | H | ethyl | H | Cl |
| | ethyl | H | ethyl | H | mercapto |
| 14 | acetyl | H | H | amino | amino |
| | acetyl | H | H | aminomethyl | aminomethyl |
| | butyryl | H | H | Br | Br |
| | butyryl | H | H | ClPhS | ClPhS |
| | succinyl | H | H | Br | Br |
| | succinyl | H | H | ClPhS | ClPhS |
| | ethyl | H | H | Cl | Cl |
| | ethyl | H | H | mercapto | mercapto |
| 15 | H | H | acetyl | amino | amino |
| | H | H | acetyl | aminomethyl | aminomethyl |
| | H | H | butyryl | Br | Br |
| | H | H | butyryl | ClPhS | ClPhS |
| | H | H | succinyl | Br | Br |
| | H | H | succinyl | ClPhS | ClPhS |
| | H | H | ethyl | Cl | Cl |
| | H | H | ethyl | mercapto | mercapto |
| 16 | acetyl | H | acetyl | amino | amino |
| | acetyl | H | acetyl | aminomethyl | aminomethyl |
| | butyryl | H | butyryl | Br | Br |
| | butyryl | H | butyryl | ClPhS | ClPhS |
| | succinyl | H | succinyl | Br | Br |
| | succinyl | H | succinyl | ClPhS | ClPhS |
| | ethyl | H | ethyl | Cl | Cl |
| | ethyl | H | ethyl | mercapto | mercapto |

Among these compounds, it is preferable to use the compound in which at least one of $R_1$, $R_2$, $R_3$, $X_1$ and $X_2$ is not a hydrogen atom in the general formula (I). Furthermore, it is preferable to use the compound in which $R_1$ and $R_3$ each is a hydrogen atom or an acyl group, $R_2$ and $X_1$ each is hydrogen atom, and $X_2$ is a hydrogen atom, a halogen atom, a sulfur-containing group, an amino group or a hydroxyl group. In case where $X_2$ is a hydrogen atom and both or one of $R_1$ and $R_3$ is an acyl group in these compounds, it is more preferable that the acyl group derived from a monocarboxylic acid have 5 to 15 carbon atoms, and the acyl group derived from a dicarboxylic acid have 2 to 15 carbon atoms. In case where $X_2$ is a halogen atom, a sulfur-containing group, an amino group or a hydroxyl group, it is also more preferable that $R_1$ and $R_2$ each be a hydrogen atom or an acyl group having 1 to 15 carbon atoms.

Among the inert carriers which may be employed in accordance with the present invention are water, ethanol, and isopropyl alcohol.

(b) FAD and Salts Thereof

FAD is known as a coenzyme of oxidation-reduction enzyme and is an important material involved in the general oxidation of organic materials in the living organisms. In addition, FAD has been widely employed as a raw material of medicines effective against diseases such as dermatitis, allergics, stomatitis and beriberi as well an effective component of eye drops.

FAD is presently produced using a fermentation technique or a synthetic method on an industrial scale and is easy to obtain as a commercial product. The salts thereof may also be used in this invention. Examples of such salts sodium salt (FAD-2Na) and potassium salt (FAD-2K).

The foregoing nucleic acid related materials (component (A)) or a combination of the component (A) and (B) (hereinafter explained in detail) used as an essential component in the composition for hair are directly applied to the scalp thereby providing a greatly improved effect of preventing graying of the hair and restoring grayed hair to its natural color hair. Such an excellent effect has never been recognized before. These materials may be incorporated into compositions for application to hair in any concentration. Although, the amount thereof to be incorporated generally varies depending on the form of the preparation and frequency of application, it is desirable to use these compounds in an amount of 0.001 to 5% by weight (hereafter referred to as %), preferably 0.01 to 2% in various compositions. When $R_1$, $R_2$, $R_3$, $X_1$, and $X_2$ of the formula (I) are hydrogen, an effective amount of the nucleic acid related substance is 0.1 to 2%. When at least one of $R_1$, $R_2$, $R_3$, $X_1$, and $X_2$ is not hydrogen, an effective amount of the nucleic acid substance is 0.01 to 2% and preferably 0.02 to 1%.

The component (B) as used herein as another essential component may be a fatty acid, a derivative thereof, an alcohol or a derivative thereof, which has an odd number of carbon atoms, as mentioned above.

The fatty (or aliphatic) acid moiety of the fatty acids and the derivatives thereof having an odd number of carbon atoms used as component (B) may be unsaturated or saturated one so far as the number of carbon atoms (chain length) constituting the carbon chain thereof is an odd number. In this connection, the unsaturated fatty acids may include a plurality of double bonds therein. Examples of such fatty acids include lower fatty acids such as propionic acid (carbon chain length=3) and valeric acid (carbon chain length=5); and higher fatty acids such as pentadecanoic acid (carbon chain length=15) and heptadecanoic acid (carbon chain length=17). Preferred are those having carbon atoms of 3 to 25, more preferably 9 to 19.

The composition for hair of the present invention may include any derivatives of these fatty acids, i.e., compounds which release an odd numbered fatty acid upon metabolization, provided that they exert no influence on human bodies. Preferred examples of derivatives of fatty acids are as follows:

a) Monoglycerides represented by the following general formulas (II) and (III):

$$\begin{array}{l} CH_2OCOR_4 \\ | \\ CH(OH) \\ | \\ CH_2(OH) \end{array} \quad (II)$$

$$\begin{array}{l} CH_2(OH) \\ | \\ CHOCOR_4 \\ | \\ CH_2(OH) \end{array} \quad (III)$$

wherein $R_4$ represents a linear organic group having an even number of carbon atoms;

b) Diglycerides represented by the following general formulas (IV) and (V):

$$\begin{array}{l} CH_2OCOR_5 \\ | \\ CHOCOR_6 \\ | \\ CH_2(OH) \end{array} \quad (IV)$$

$$\begin{array}{l} CH_2OCOR_5 \\ | \\ CH(OH) \\ | \\ CH_2OCOR_6 \end{array} \quad (V)$$

wherein $R_5$ and $R_6$ represent a chain organic group with the proviso that at least one of them is a linear organic group having carbon atoms of an even number;

c) Triglycerides represented by the following general formula (VI):

$$\begin{array}{l} CH_2OCOR_5 \\ | \\ CHOCOR_6 \\ | \\ CH_2OCOR_7 \end{array} \quad (VI)$$

wherein $R_5$, $R_6$ and $R_7$ are respectively a chain organic group with the proviso that at least one of them is a linear organic group having an even number of carbon atoms;

d) Fatty acid salts represented by the following general formula (VII):

$$(R_4COO)_n M_2 \quad (VII)$$

wherein $R_4$ is the same as defined above, $M_2$ represents a metal atom and n is an integer corresponding to the valency of $M_2$;

e) Esters represented by the following general formula (VIII):

$$R_4COOR_8 \quad (VIII)$$

wherein $R_4$ is the same as defined above and $R_8$ represents a monovalent or bivalent alcohol residue, an amine residue, a polyoxyethylene residue, a sorbitan residue or a sucrose residue;

f) Primary amides represented by the following general formula (IX):

$$R_4CONR_9R_{10} \quad (IX)$$

wherein $R_4$ is the same as defined above and $R_9$ and $R_{10}$, respectively, represent hydrogen atom or an organic group;

g) Secondary amides represented by the following general formula (X):

$$R_5CON(R_9)COR_6 \quad (X)$$

wherein $R_5$ and $R_6$ are the same as those defined above in connection to compounds (IV) or (V) and $R_9$ is the same as defined above;

h) Tertially amides represented by the following general formula (XI):

$$R_5CONCOR_6 \atop COR_7 \qquad (XI)$$

wherein $R_5$, $R_6$ and $R_7$ are the same as defined above;

i) Dibasic acids and salts thereof represented by the following general formula (XII):

$$HOOCR_{11}COOH \qquad (XII)$$

wherein $R_{11}$ represents a linear organic group having an odd number of carbon atoms;

j) Sterol esters represented by the following general formula (XIII):

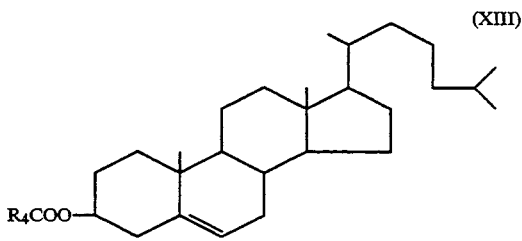

(XIII)

wherein $R_4$ is the same as defined above;

k) Phospholipids represented by the following general formula (XIV):

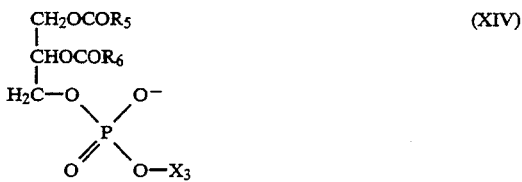

(XIV)

wherein $R_5$ and $R_6$ are the same as defined above and $X_3$ represents a choline residue, an ethanolamine residue, a serine residue or an inositol residue;

l) Phosphatidic acids represented by the following general formula (XV):

(XV)

wherein $R_5$ and $R_6$ are the same as defined above; and m) Sphingolipids represented by the following general formula (XVI):

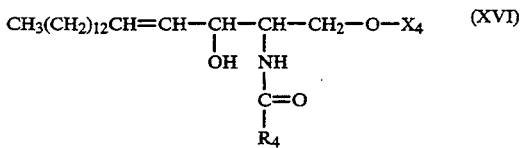

(XVI)

wherein $R_4$ is the same as that defined above and $X_4$ is a residue, a phosphate residue or an amine base residue.

In the above general formulas, $R_4$ is preferably the linear organic group having 2 to 24, more preferably 8 to 18. At least one of $R_5$ and $R_6$ in the formulas (IV), (V), (XIV) and (XV) is the chain organic group having an even number of carbon atoms (preferably 2 to 24 and more preferably 8 to 18) and it is particularly preferred that both of them represent those having an even number of carbon atoms.

At least one of $R_5$ to $R_7$ in the formula (VI) and (XI) is the chain organic group having carbon atoms of even number, preferably 2 to 24, more preferably 8 to 18 and it is particularly preferred that all the substituents $R_5$ to $R_7$ are those having even number of carbon atoms falling within foregoing range.

In $R_8$ of the formula (VIII), examples of the monovalent alcohol group include those having 1 to 18 carbon atoms such as methanol and ethanol residues and examples of the amine residues include mono-, di- and triethanolamines.

As the organic groups represented by $R_9$ and $R_1{}^0$ in the formulas (IX) and (X), alkyl groups having 1 to 18 carbon atoms As the organic groups represented by $R_9$ and $R_1{}^0$ in the formulas (IX) and (X), alkyl groups having 1 to 18 carbon atoms such as methyl and ethyl groups are preferred. Preferred examples of $R_{11}$ in the formula (XII) include hydrocarbon residues having 1 to 23 carbon atoms (more preferably 1 to 17) such as methylene groups.

In the formula (XIV), if $X_3$ is a choline residues the compound is phosphatidyl choline, if it is an ethanolamine residue, compound (XIV) is phosphatidyl ethanolamine, if it is a serine residue, the compound is phosphatidyl serine and if it represents an inositol residue, the compound is phosphatidyl inositol. Moreover, examples of $M_2$ in the formula (VII) include an alkali metal such as sodium, potassium and lithium.

In the composition of the present invention, the components (B) listed above may be incorporated thereinto alone or in combination and concrete examples thereof are fatty acids such as nonanoic acid, tridecanoic acid and pentadecanoic acid: monoglycerides such as glyceryl monotridecanoate, glyceryl monopentadecanoate and glyceryl monoheptadecanoate; diglycerides such as glyceryl diundecanoate, glyceryl ditridecanoate and glyceryl dipentadecanoate; triglycerides such as glyceryl trinonanoate, glyceryl tritridecanoate, glyceryl tripentadecanoate and diacetylglyceryl monopentadecanoate; fatty acid salts such as potassium nonanoate and sodium pentadecanoate; esters such as ethyl pentadecanoate and methyl nonadecanoate; primary amides such as pentadecanoyl amide; secondary amides such as N-acetylpentadecanoyl amide; tertially amides such as N,N-diacetylpentadecanoyl amide; dibasic acids and the salts thereof such as 1,13-tridecamethylenedicarboxylic acid; sterol esters such as choresterol pentadecanoate; phospholipids such as 1,2-dipentadecanoyl-glycero-3-phosphorylcholine; phosphatidic acids such as 1,2-dipentadecanoyl-glycero-3-phosphoric acid; and sphingolipids such as N-pentadecanoylsphingosine-1-phosphorylethanolamine.

The alcohols usable as component (B) may be saturated or unsaturated ones with the proviso that the number of carbon atoms constituting the carbon chain thereof is an odd number. Such unsaturated alcohols may include a plurality of double bonds therein. Examples thereof include lower alcohols such as propyl alcohol (chain length=3) and amyl alcohol (chain length=5) and higher alcohols such as tricosyl alcohol (chain length=23) and pentacosyl alcohol (chain length=25). In addition, the hydroxyl group may be bonded to any carbon atom of the carbon chain. Among these, preferred are those having 3 to 25 (more preferably 9 to 19) carbon atoms.

The derivatives of the alcohols listed above may be used herein and exemplary derivatives are esters and ethers of the alcohols having an odd number of carbon atoms.

Such an ester is represented by the following general formula:

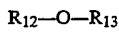

wherein $R_{12}$ represents an alcohol residue having an odd number (preferably 3 to 25, more preferably 9 to 19) of carbon atoms and $R_{13}$ a residue of organic acid such as an aliphatic acid residue (preferably having 2 to 24 carbon atoms), succinic acid, citric acid, fumalic acid, lactic acid, pyruvic acid, malic acid and oxaloacetic acid; and residues of inorganic acids such as phosphoric acid.

Examples of such ethers as used herein are represented by the following general formula:

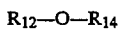

wherein $R_{12}$ is the same as defined above and $R_{14}$ represents a monovalent alcohol residue (preferably having 2 to 24 carbon atoms); a residue of polyvalent alcohol such as glycerin, polyglycerin, ethylene glycol, propylene glycol and butanediol; or a residue of sugar such as dextrose, ribose, galactose, arabinose, mannose, xylose, sorbitol and mannitol. These ethers may have 2 or more of alcohol residues having an odd number of carbon atoms such as di- or trialkoxide (having an odd number of carbon atoms) of glycerin in a molecule.

The only requirement for the alcohol derivatives having an odd number of carbon atoms as used herein is to have alcohol residue(s) having an odd number of carbon atoms. Therefore, the acid residues in the aforementioned esters may be substituted with a variety of substituents and likewise the alcohol residues other than the former and the sugar residues of the ethers may be substituted with various substituents. In this respect, it is a matter of course that these residues and the substituents therefor should not exert any influence on human bodies.

Specific examples of these alcohols or derivatives thereof include undecyl alcohol, tridecyl alcohol, pentadecyl alcohol, heptadecyl alcohol, nonyl acetate, undecyl succinate, pentadecyl citrate, triundecyl glycerylether and tripentadecyl glycerylether and they may be used alone or in combination.

The component (B) may be incorporated into the composition for hair of the present invention in any amount or concentration. In general, the amount thereof in the composition approximately ranges from 0.01 to 20%, preferably 0.1 to 10%. In addition, the weight ratio of the component (A) to the component (B) is preferably in the range of from 1/100 to 10/1.

In addition to the foregoing components, the composition of this invention may further comprise other pharmaceutical components such vitamins as vitamin A, vitamin $B_6$, vitamin E, pantothenic acid and biotin; such amino acids as methionine, cysteine, cystine and tyrosine; such antibacterial agents as salicylic acid, hinokitiol, resorcin and trichlorocarbanilide; and such hormones as ethynylestradiol and progesterone and these pharmaceutical components are preferably added to compositions for hair in an amount of 0.0001 to 3%.

Moreover, other materials commonly used in cosmetics can also be added to the composition for hair of the present invention and examples thereof include oils, water, surfactants, humectants, lower alcohols, thickening agents, antioxidants, chelating agents, pH-adjusting agents, preservatives, perfumes and color additives. Examples of oils include fats and oils such as olive oil, jojoba oil and hardened oil; waxes such as spermaceti, beeswax and lanolin; hydrocarbons such as liquid paraffin, ceresin and squalane; fatty acids such as stearic acid and oleic acid; alcohols such as cetanol, stearyl alcohol, lanolin alcohol and hexyl decanol; and esters such as isopropyl myristate and butyl stearate. These oils are incorporated into the composition for hair alone or in combination and the amount thereof ranges from 0.5 to 85%.

Examples of surfactants are anionic surfactants such as sodium stearate, sodium cetylsulfate, polyoxyethylene laurylether phosphate and sodium N-acyl glutamate; cationic surfactants such as stearyldimethylbenzylammonium chloride and stearyltrimethylammonium chloride; amphoteric surfactants such as alkylaminoethylglycine hydrochloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxyethylene polyoxypropylene glycol, polyoxyethylene castor oil and polyoxyethylene lanolin. These surfactants may be used in the composition for hair alone or in combination and the amount thereof falls within the range of 0.1 to 15%.

Moreover, there may be mentioned such humectants as glycerin, 1,3-butylene glycol and propylene glycol; such lower alcohols as ethanol and isopropanol; such thickening agents as polyethylene glycol and sodium carboxymethylcellulose; such antioxidants as dibutylhydroxytoluene, butylhydroxyanisole and propyl gallate; such chelating agents as disodium edetate and ethanehydroxy diphosphate; such pH-adjusting agents as citric acid, sodium citrate, boric acid, borax and disodium hydrogen phosphate; and such preservatives as methyl parahydroxybenzoate, ethyl para-hydroxybenzoate, dehydroacetic acid, salicylic acid and benzoic acid.

In this respect, these optional components are not restricted to those specific examples listed above.

The compositions for hair of the present invention may be prepared by appropriately admixing the foregoing essential components and optional components and may be used in any forms capable of external use such as hair tonics, creams, lotions, milky lotions and ointments. For instance, hair tonics comprise 0.01 to 2% of the essential components (component (A)) of the present invention, 40 to 98% of a lower alcohol, 0 to 3% of the foregoing pharmaceutical component, 0 to 15% of a humectant, 0 to 60% of purified water and a small amount of a perfume; or comprise 0.01 to 2% of the essential component (A), 0.1 to 10% of the component (B), 40 to 98% of a lower alcohol, 0 to 3% of the foregoing pharmaceutical component, 0 to 15% of a humectant, 0 to 60% of purified water and a small amount of a perfume; hair creams comprise 0.01 to 2% of the essential component (A) of the present invention, 20 to 80% of an oil, 0.5 to 15% of a surfactant, 0 to 15% of a humectant, 15 to 80% of purified water and a small amount of a preservative; or comprise 0.01 to 2% of the essential component (A), 0.1 to 10% of the component (B), 20 to 80% of an oil, 0.5 to 15% of a surfactant, 0 to 15% of a humectant, 15 to 80% of purified water and a small amount of a preservative; and milky lotions comprise 0.01 to 2% of the essential component (A) of the present invention, 5 to 30% of an oil, 0.5 to 15% of a surfactant, 0 to 15% of a humectant, 50 to 95% of purified water and a small amount of a preservative; or comprise 0.01 to 2% of the essential component (A), 0.1 to 10% of the component (B), 5 to 30% of an oil, 0.5 to 15% of a surfactant, 0 to 15% of a humectant, 50 to 95% of purified water and a small amount of a preservative.

Although, the reason why the nucleic acid related substances (component (A)) or a combination of the components (A) and (B) exhibit such an excellent effect of preventing graying of the hair and restoring grayed hair to its natural color has not yet been clearly evidenced, it is assumed that, when externally applied, the melanocytes present in the bulbus pili of the scalp radix pili are activated to promote the synthesis of melanin and the resultant melanin granules are promoted to be incorporated into mother cells of the hair.

The aforementioned nucleic acid related substances as used herein are naturally present in a wide range of the living organisms and, therefore, are considered to be highly safe. When the level of safety was checked in order to make sure, no practical problem was observed with respect to acute toxicity, skin irritation or skin sensitization and thus a high level of safety was confirmed. Likewise, when the components (A) and (B) were used in combination, no practical problems regarding safety were observed.

In accordance with the present invention, a composition for hair capable of preventing graying of the hair and restoring grayed hair to its natural color upon externally applied to the scalp is provided. Besides, the composition is highly safe as regards the possibility of causing skin damage.

Therefore, the composition according to the present invention can be widely used in various forms capable of being externally applied. Such forms include, for example, cosmetic compositions such as hair tonics, creams, lotions, milky lotions, hair treatments, hair conditioners and ointments.

Furthermore, if the components (A) and (B) are simultaneously incorporated in the composition of the present invention, the foregoing effects can further be enhanced.

The present invention will hereunder be explained in more detail with reference to the following non-limitative working examples. Moreover, the effects practically attained according to the invention will also be discussed with reference to comparative examples.

The abbreviations given below are used in the examples

MB: monobutyryl
MH: monohexanoyl
MO: monooctanoyl
MS: monosuccinyl
DA: diacetyl
DB: dibutyryl
DM: dimalonyl
DS: disuccinyl
clPhS: 4-chlorophenylthio In the examples, the position of the substituent of the cAMP derivatives is shown as follows:

$N^6$: Binding position of $R_1$ or $R_2$ is indicated except that $R_1$ or $R_2$ is not a hydrogen atom.

$O^{2'}$: Binding position of $R_3$ is indicated except that $R_3$ is not a hydrogen atom.

8: Binding position of $X_2$ is indicated except that $X_2$ is not a hydrogen atom.

EXAMPLE 1

A perfume was uniformly dissolved in ethanol. In addition, a solution was prepared by uniformly dissolving other components listed below in purified water. Then, the ethanollic solution was added to the aqueous solution to form a hair tonic. Details are shown in Table II wherein each numerical value represents loadings expressed as % by weight (the same in all tables hereafter).

TABLE II

| Component | Present Invention | Comparative Example |
|---|---|---|
| Ethanol | 80.0 | 80.0 |
| Glycerin | 0.5 | 0.5 |
| $N^6,O^{2'}$-DBcAMP-Na | 0.05 | — |
| Color Additive | small amount | small amount |
| Perfume | " | " |
| Purified Water | 19.45 | 19.5 |

The effectiveness of the hair tonics thus prepared were estimated in the following manner:

Twenty statistically equivalent persons (comprising men and women aged 30 to 60 years) were selected and Samples of the hair tonics were applied to their scalps in accordance with the Half-Head technique, in which Samples were separately applied to the right and left half portions of the scalp, twice a day (in the morning and at night) for three months. The effects of preventing graying of the hair and restoring grayed hair to its natural color were estimated by comparing the conditions of the portions observed before and after the application of Samples. The results obtained are summarized in the following Table III.

TABLE III

| This Invention is better | This Invention is somewhat better | Same | Comp. Sample is somewhat better | Comp. Sample is better |
|---|---|---|---|---|
| 11 | 7 | 2 | 0 | 0 |

As seen from the results shown in Table III, it was found that the hair tonic of the invention comprising $N^6,O^{2'}$-DBcAMP-Na reduced the amount of grayed hair more effectively than the comparative hair tonic free from such component and that the former showed remarkable effect of preventing graying of the hair and restoring grayed hair to its natural color.

No abnormality was observed in the condition of the scalp during and after the use of the hair tonic of the invention for 3 months. Safety tests on $N^6,O^{2'}$-DBcAMP-Na were conducted. The results observed are summarized in Table IV.

TABLE IV

| Items Examined | Results Observed |
|---|---|
| Acute Oral Toxicity (rat) | $LD_{50}$ = 5 g/kg or more |
| Skin Irritating Property | |
| 1) Primary Skin Irritation (guinea pig) | 5%: non-irritant |
| 2) Phototoxicity (guinea pig) | negative |

TABLE IV-continued

| Items Examined | Results Observed |
|---|---|
| 3) Ocular-mucous Membrane Irritation (rabbit) | 5%: non-irritant |
| Skin Sensitizing Property | |
| 1) Skin Sensitization (guinea pig) | negative |
| 2) Photosensitization (guinea pig) | negative |
| Human Patch Test | 5%: non-irritant |

The results in Table IV show that the safety of $N^6,O^{2'}$-DBcAMP-Na is extremely high.

EXAMPLE 2

Hair creams were prepared by separately dissolving components 1 to 6 and components 7 to 10 listed in Table V while heating at 80° C., then mixing and emulsifying these solutions, adding component 11 during cooling and uniformly dispersing the mixture.

TABLE V

| Components | Present Invention | Comp. Sample |
|---|---|---|
| 1. Lanolin | 2.5 | 2.5 |
| 2. Sorbitan Monostearate | 5.0 | 5.0 |
| 3. Polyoxyethylene Sorbitan Monostearate (EO P = 20)* | 2.0 | 2.0 |
| 4. Beeswax | 10.0 | 10.0 |
| 5. Liquid Paraffin | 22.0 | 22.0 |
| | 23.0 | 23.0 |
| 6. Hardened Oil | | |
| 7. Ethyl Parahydroxybenzoate | 0.2 | 0.2 |
| 8. Borax | 0.5 | 0.5 |
| 9. $N^6,O^{2'}$-DScAMP-Na | 0.1 | — |
| 10. Purified Water | 34.2 | 34.3 |
| 11. Perfume | 0.5 | 0.5 |

*Average number of ethylene oxide adducted (hereinafter referred to as EO P).

According to the procedures disclosed in Example 1, these hair creams were examined on the effects of preventing graying of the hair and restoring grayed hair to its natural color. Results are summarized in Table VI.

TABLE VI

| This Invention is better | This Invention is somewhat better | Same | Comp. Sample is somewhat better | Comp. Sample is better |
|---|---|---|---|---|
| 10 | 8 | 2 | 0 | 0 |

As seen from the results listed in Table VI, the hair cream of the present invention containing $N^6,O^{2'}$-DScAMP-Na exhibits an excellent effect of preventing graying of the hair and restoring grayed hair to its natural color as compared with the comparative hair cream free from the component and thus the amount of grayed hair was reduced.

In addition, during and after the use of the hair cream of the invention for 3 months, no abnormality was observed in the condition of the scalp. According to the same procedures as in Example 1, the safety of $N^6,O^{2'}$-DScAMP-Na was examined and it was confirmed that it had no problems such as skin irritation and thus had extremely high safety.

EXAMPLE 3

Milky lotions were prepared by separately dissolving components 1 to 4 and components 5 to 9 listed in Table VII and then adding the solution of the components 1 to 4 to that of the components 5 to 9 with stirring.

TABLE VII

| Components | Present Invention | Comp. Sample |
|---|---|---|
| 1. Lanolin Alcohol | 5.0 | 5.0 |
| 2. Isopropyl Myristate | 2.0 | 2.0 |
| 3. Stearic Acid | 5.0 | 5.0 |
| 4. Glycerin Monostearate | 1.0 | 1.0 |
| 5. Triethanolamine | 1.0 | 1.0 |
| 6. Propylene Glycol | 5.0 | 5.0 |
| 7. $O^{2'}$-MScAMP-Na | 0.2 | — |
| 8. Preservative | small amount | small amount |
| 9. Purified Water | 80.8 | 81.0 |

According to the procedures described in Example 1, these lotions were examined on the effects of preventing graying of the hair and restoring grayed hair to its natural color. Results are summarized in Table VIII.

TABLE VIII

| This Invention is better | This Invention is somewhat better | Same | Comp. Sample is somewhat better | Comp. Sample is better |
|---|---|---|---|---|
| 10 | 7 | 3 | 0 | 0 |

As seen from the results listed in Table VIII, the milky lotion of the present invention containing $O^{2'}$-MScAMP-Na exhibits an excellent effect of preventing graying of the hair and restoring grayed hair to its natural color as compared with the comparative milky lotion free from the component and thus the amount of grayed hair was reduced.

In addition, during and after the use of the milky lotion of the invention for 3 months, no abnormality was observed in the condition of the scalp. According to the same procedures as in Example 1, the safety of $O^{2'}$-MScAMP-Na was examined and it was confirmed that it had no problems such as skin irritation and thus had extremely high safety.

EXAMPLE 4

Hair creams having compositions shown in Table IX were prepared and the effect of preventing graying of the hair and restoring grayed hair to its natural color was examined. Results observed are listed in Table IX.

TABLE IX

| Components | Present Invention | Comp. Sample |
|---|---|---|
| Cetanol | 25.0 | 25.0 |
| White Vaseline | 25.0 | 25.0 |
| Polyethyleneglycol Monostearate (EO P = 40) | 5.0 | 5.0 |
| Propylene Glycol | 12.0 | 12.0 |
| $N^6$-MBcAMP-Na | 0.8 | — |
| Preservative | small amount | small amount |
| Purified Water | 32.2 | 33.0 |

TABLE X

| This Invention is better | This Invention is somewhat better | Same | Comp. Sample is somewhat better | Comp. Sample is better |
|---|---|---|---|---|
| 9 | 7 | 4 | 0 | 0 |

As seen from the results listed in Table X, the hair cream of the present invention containing $N^6$-MBcAMP-Na exhibits an excellent effect of preventing graying of the hair and restoring grayed hair to its natural color as compared with the comparative hair cream free from the component and thus the amount of grayed hair was reduced.

In addition, during and after the use of the hair cream of the invention for 3 months, no abnormality was observed in the condition of the scalp. According to the same procedures as in Example 1, the safety of $N^6$-MBcAMP-Na was examined and it was confirmed that it had no problems such as skin irritation and thus had extremely high safety.

EXAMPLE 5

The procedures of Example 2 were repeated except that 8-BrcAMP-Na, 8-ClcAMP-Na, 8-ClPhScAMP-Na, 8-SHcAMP-Na, 8-OHcAMP-Na, $O^{2'}$-MB-8BrcAMP-Na or $N^6,O^{2'}$-DA-8-NH$_2$cAMP-Na was used instead of $N^6,O^{2'}$-DScAMP-Na to form hair creams and the aforesaid effect was also estimated according to the same manner as in Example 1. Substantially the same excellent effect as in Example 2 was observed.

EXAMPLE 6

Components shown in Table XI other than ethanol were in order dissolved in ethanol to form hair tonics (Samples S-I to S-III). Composition of each Sample was shown in Table XI.

| Component | Present Invention S-I | Present Invention S-II | Comp. Example S-III |
| --- | --- | --- | --- |
| Ethanol | 97.45 | 99.45 | 99.5 |
| Glycerin | 0.5 | 0.5 | 0.5 |
| $N^6,O^{2'}$-DBcAMP-Na | 0.05 | 0.05 | — |
| Glyceryl Monopentadecanoate | 2.0 | — | — |
| Color Additive | small amount | small amount | small amount |
| Perfume | " | " | " |

Two groups each of which comprised 20 persons (50 to 60 years old; comprising men and women) were selected and the hair tonic Samples (S-I and S-II) were separately applied to scalp of each person of one group in accordance with Half-Head technique wherein the hair tonics I and II were separately applied to the right half of the scalp and the left half thereof, on the other hand Samples (S-II and S-III) were likewise separately applied to each person of the other group in the same manner twice a day (in the morning and at night) for 3 months. Then, the effects of preventing graying of the hair and restoring grayed hair to its natural color were estimated by comparing the conditions of the portions observed before and after the application of Samples and the results obtained were listed in Tables XII and XIII.

TABLE XII

| This Invention (S-II) is better | This Invention (S-II) is somewhat better | Same | Comp. Sample (S-III) is somewhat better | Comp. Sample (S-III) is better |
| --- | --- | --- | --- | --- |
| 7 | 8 | 5 | 0 | 0 |

TABLE XIII

| This Invention (S-I) is better | This Invention (S-I) is somewhat better | Same | This Invention (S-II) is somewhat better | This Invention (S-II) is better |
| --- | --- | --- | --- | --- |
| 3 | 8 | 7 | 2 | 0 |

It is confirmed that Samples S-I and S-II according to the present invention are excellent in the effects of preventing graying of the hair and restoring grayed hair to its natural color compared with the comparative example (Sample S-III). This is the very effects due to the incorporation of $N^6, O^{2'}$-DBcAMP-Na or the combination of it with glyceryl monopentadecanoate into the hair tonics. Moreover, the effect of S-I is superior to that of S-II. This means that the addition of the component (B) is effective to further improve the aforesaid effect.

In addition, during and after the application of the hair tonics of the invention for 3 months, no abnormality was observed in the condition of the scalp.

EXAMPLE 7

Hair creams (H-I to H-III) were prepared by separately dissolving components 1 to 6 and components 7 to 10 listed in Table XIV while heating at 80° C., then admixing and emulsifying these solutions, adding component 11 thereto during cooling and uniformly dispersing the mixture.

TABLE XIV

| Components | Present Invention (H-I) | Present Invention (H-II) | Comp. Example (H-III) |
| --- | --- | --- | --- |
| 1. Beeswax | 10.0 | 10.0 | 10.0 |
| 2. Spermaceti | 5.0 | 5.0 | 5.0 |
| 3. Hardened Oil | 19.5 | 19.5 | 19.5 |
| 4. Liquid Paraffin | 35.0 | 35.0 | 35.0 |
| 5. Antioxidant | small amount | small amount | small amount |
| 6. Glyceryl Triheptadecanoate | 1.5 | — | — |
| 7. cAMP-Na | 0.1 | 0.1 | — |
| 8. Borax | 0.5 | 0.5 | 0.5 |
| 9. Preservative | small amount | small amount | small amount |
| 10. Purified Water | 28.4 | 29.9 | 30.0 |
| 11. Perfume | small amount | small amount | small amount |

According to the same procedures as those in Example 6, these hair creams were examined on the effect of preventing graying of the hair and restoring grayed hair to its natural color and results obtained were listed in Tables XV and XVI.

TABLE XV

| This Invention (H-II) is better | This Invention (H-II) is somewhat better | Same | Comp. Sample (H-III) is somewhat better | Comp. Sample (H-III) is better |
| --- | --- | --- | --- | --- |
| 6 | 7 | 7 | 0 | 0 |

TABLE XVI

| This Invention (H-I) is better | This Invention (H-I) is somewhat better | Same | This Invention (H-II) is somewhat better | This Invention (H-II) is better |
| --- | --- | --- | --- | --- |
| 4 | 7 | 6 | 3 | 0 |

It is confirmed that Samples H-I and H-II according to the present invention are excellent in the effects of preventing graying of the hair and restoring grayed hair to its natural color compared with the comparative example (Sample H-III) as seen from the results on Tables XV and XVI. This is the very effects due to the incorporation of cAMP-Na or the combination of it with glyceryl triheptadecanoate into the hair creams. Moreover, the effect of H-I is superior to that of H-II. This means that the addition of the component (B) is effective to further improve the aforesaid effect.

In addition, during and after the application of the hair creams of the invention for 3 months, no abnormality was observed in the condition of the scalp.

EXAMPLE 8

Components shown in Table XVII other than ethanol were in order dissolved in ethanol to form Samples I to III (hereunder referred to as S-I to S-3) of hair tonic. The composition of each Sample is shown in Table XVII.

TABLE XVII

| Component | Present Invention S-1 | Present Invention S-2 | Comp. Example S-3 |
| --- | --- | --- | --- |
| Ethanol | 86.5 | 89.5 | 89.6 |
| Castor Oil | 10.0 | 10.0 | 10.0 |
| Hinokitiol | 0.1 | 0.1 | 0.1 |
| Alpha-tocopherol | 0.3 | 0.3 | 0.3 |
| $N^6, O^{2'}$-DScAMP-Na | 0.1 | 0.1 | — |
| Pentadecyl Alcohol | 3.0 | — | — |
| Color Additive | small amount | small amount | small amount |
| Perfume | small amount | small amount | small amount |

According to Example 6, the hair tonics were examined on the effect of preventing graying of the hair and restoring grayed hair to its natural color and results obtained are listed in Tables XVIII and XIX.

TABLE XVIII

| This Invention (S-2) is better | This Invention (S-2) is somewhat better | Same | Comp. Sample (S-3) is somewhat better | Comp. Sample (S-3) is better |
| --- | --- | --- | --- | --- |
| 8 | 7 | 5 | 0 | 0 |

TABLE XIX

| This Invention (S-1) is better | This Invention (S-1) is somewhat better | Same | This Invention (S-2) is somewhat better | This Invention (S-2) is better |
| --- | --- | --- | --- | --- |
| 5 | 6 | 6 | 3 | 0 |

It is confirmed that Samples S-1 and S-2 according to the present invention are excellent in the effects of preventing graying of the hair and restoring grayed hair to its natural color compared with the comparative example (Sample S-3) as seen from the results in Tables XVIII and XIX. This is the very effects due to the incorporation of $N^6, O^{2'}$-DScAMP-Na or the combination of it with pentadecyl alcohol into the hair tonics. Moreover, the effect of S-1 is superior to that of S-2. This means that the addition of the component (B) is effective to further improve the aforesaid effect.

In addition, during and after the application of the hair tonics of the invention for 3 months, no abnormality was observed in the condition of the scalp.

EXAMPLE 9

Milky lotions for hair (L-1 to L-3) were prepared by separately dissolving components 1 to 6 and components 7 to 11 listed in Table XX while heating at 80° C., then admixing and emulsifying these solutions, adding component 12 thereto during cooling and uniformly dispersing the mixture.

TABLE XX

| Components | Present Invention (L-1) | Present Invention (L-2) | Comp. Example (L-3) |
| --- | --- | --- | --- |
| 1. Stearic Acid | 2.5 | 2.5 | 2.5 |
| 2. Cetanol | 1.5 | 1.5 | 1.5 |
| 3. Vaseline | 5.0 | 5.0 | 5.0 |
| 4. Liquid Paraffin | 10.0 | 10.0 | 10.0 |
| 5. Polyethylene Glycol (EO P = 6) Monooleate | 2.0 | 2.0 | 2.0 |
| 6. Tridecyl Acetate | 2.5 | — | — |
| 7. FAD-2Na | 0.5 | 0.5 | — |
| 8. Polyethylene Glycol 1500 | 3.0 | 3.0 | 3.0 |
| 9. Triethanolamine | 1.0 | 1.0 | 1.0 |
| 10. Preservative | small amount | small amount | small amount |
| 11. Purified Water | 72.0 | 74.5 | 75.0 |
| 12. Perfume | small amount | small amount | small amount |

According to the same procedures as those in Example 6, these milky lotions for hair were examined on the effect of preventing graying of the hair and restoring grayed hair to its natural color and results obtained are listed in Tables XXI and XXII.

TABLE XXI

| This Invention (L-2) is better | This Invention (L-2) is somewhat better | Same | Comp. Sample (L-3) is somewhat better | Comp. Sample (L-3) is better |
| --- | --- | --- | --- | --- |
| 7 | 7 | 6 | 0 | 0 |

TABLE XXII

| This Invention (L-1) is better | This Invention (L-1) is somewhat better | Same | This Invention (L-2) is somewhat better | This Invention (L-2) is better |
| --- | --- | --- | --- | --- |
| 4 | 8 | 6 | 2 | 0 |

It is confirmed that Samples L-1 and L-2 according to the present invention are excellent in the effects of preventing graying of the hair and restoring grayed hair to its natural color compared with the comparative example (Sample L-3) as seen from the results in Tables XXI and XXII. This is the very effects due to the incorporation of FAD-2Na or the combination of it with tridecyl acetate into the milky lotion for hair. Moreover, the effect of L-1 is superior to that of L-2. This means that the addition of the component (B) is effective to further improve the aforesaid effect.

In addition, during and after the application of the milky lotions for hair of the invention for 3 months, no abnormality was observed in the condition of the scalp.

Moreover, the same milky lotion (L-2 and L-3) were examined on hair growing effect in the following manner:

After removing hair from the back to both sides of the abdomen of each mouse in groups each of which comprised 6 C57 black mice, the milky lotion of the invention was applied to one half of the portion from which hair was removed and the comparative example was applied to the other half thereof once a day for 2 weeks. Then, the length of freshly growing hair was determined every week and the hair growth promoting effect was estimated by comparing the measured length of hair. Results observed are listed in Table XXIII in which each numerical value is the length of hair (mm) expressed as averaged value±standard deviation.

TABLE XXIII

|  | Present Invention | Comp. Example |
| --- | --- | --- |
| After 1 Week | 2.0 ± 0.2 | 1.1 ± 0.1 |
| After 2 Weeks | 6.3 ± 0.6 | 3.1 ± 0.5 |

As seen from the results listed in Table XXIII, the milky lotion (L-2) of the present invention containing FAD-2Na exhibits an excellent hair growing effect as compared with the comparative milky lotion free from FAD-2Na.

According to the same procedures as in Example 1, the safety of FAD-2Na was examined and it was confirmed that it had no problems such as skin irritation and thus had extremely high safety.

EXAMPLE 10

The procedures of Example 7 were repeated except that cAMP-Na used therein was replaced with $O^2$-MBcAMP-Na or FAD to obtain hair creams and they were likewise examined on the aforementioned effect. As a result, approximately the same results as those in Example 7 were obtained.

EXAMPLE 11

The procedures in Example 7 were repeated except that glyceryl triheptadecanoate was replaced with tri-undecyl glycerylether or nonanoic acid. The resulting hair creams were examined on the aforesaid effects and approximately the same results as in Example 7 were obtained.

EXAMPLE 12

Components shown in Table XXIV other than ethanol were in order dissolved in ethanol to form hair tonics. The composition of each hair tonic is shown in Table XXIV.

TABLE XXIV

|  | Present Invention | Comp. Example |
| --- | --- | --- |
| Ethanol | 75.0 | 75.0 |
| Olive Oil | 0.5 | 0.5 |
| Pyrrolidone Carboxylic Acid | 0.5 | 0.5 |
| FAD-2Na | 0.1 | — |
| Perfume | small amount | small amount |
| Purified Water | 23.9 | 24.0 |

According to Example 1, the hair tonics were examined on the effect of preventing graying of the hair and restoring grayed hair to its natural color and results obtained are listed in Table XXV.

TABLE XXV

| This Invention is better | This Invention is somewhat better | Same | Comp. Sample is somewhat better | Comp. Sample is better |
| --- | --- | --- | --- | --- |
| 8 | 8 | 4 | 0 | 0 |

It is confirmed that the hair tonic of the present invention is excellent in the effects of preventing graying of the hair and restoring grayed hair to its natural color compared with the comparative example as clear from Table XXV. In addition, during and after the application of the hair tonics of the invention for 3 months, no abnormality was observed in the condition of the scalp.

EXAMPLE 13

The procedures in Example 12 were repeated except that $N^6$-MScAMP-Na, $N^6$-MHcAMP-Na $O^{2'}$-MOcAMP-Na or $N^6,O^{2'}$-DMcAMP-Na was used in place of FAD-2Na used in Example 12 to form hair tonics and the properties thereof were estimated in accordance with the same manner as in Example 1. Thus, it is confirmed that these hair tonics likewise provide substantially the same effect as in Example 12.

EXAMPLE 14

The procedure of Example 8 were repeated except that glyceryl ditridecanoate, dicetylglyceryl monopentadecanoate, sodium nonadecanoate, methyl heptadecanoate, tridecanoyiamide, N-acetylundecanoylamide, N,N-diacetylnonanoylamide, 1,13-tridecamethylenedicarboxylic acid, choresterol nonanoate, 1,2-diundecanoyl-glycero-3-phosphorylcoline, 1,2-dipentadecanoyl-glycero-3-phosphoric acid or N-tridecanoylsphingosine-1-phosphoryl-ethanolamine was used instead of pentadecyl alcohol and 8-clPhScAMP-Na was used instead of $N^6,O^{2'}$-DScAMP-Na to form hair tonics, and the aforesaid effect was also estimated according to the same manner as in Example 8.

As a result, substantially the same excellent effect as in Example 8 was obtained.

EXAMPLE 15

The procedures of Example 1 were repeated except that $N^6$, $O^{2'}$-DBcAMP-Na was used in an amount of 0.01% or 0.005% instead of 0.05% to prepare hair tonics, and the effects of preventing graying of the hair and restoring grayed hair to its natural color were estimated according to the same manner as in Example 1.

The results are shown in Table XXVI. In this Table, Comp. Sample does not contain $N^6, O^{2'}$—DBcAMP-Na.

TABLE XXVI

| No. | Thus obtained hair tonic is better | Thus obtained hair tonic somewhat better | Same | Comp. Sample is somewhat better | Comp. Sample is better |
|---|---|---|---|---|---|
| A* | 2 | 8 | 9 | 1 | 0 |
| B* | 0 | 4 | 14 | 2 | 0 |

A* Content of $N^6,O^{2'}$—DBcAMP-Na is 0.01%
B* Content of $N^6,O^{2'}$—DBcAMP-Na is 0.005%

As is clear from Table XXVI, the composition containing $N^6, O^{2'}$—DBcAMP-Na in an amount of 0.01 is effective in preventing graying of the hair and restoring grayed hair to its natural color, although the composition containing the same in an amount of 0.005% has little effect.

COMPARATIVE EXAMPLE

The procedures of Example 7 were repeated except that cAMP-Na was used in an amount of 0.01% instead of 0.1 of hair cream (H-II) to prepare Comp. Sample H-IV, and the effects of preventing graying of the hair and restoring grayed hair to its natural color were estimated according to the same manner as in Example 1.

The results are in table XXVII, in this Table. Comp. Sample H-III does not contain cAMP-Na.

TABLE XXVIII

| Comp. Sample H-IV is better | Comp. Sample H-IV is somewhat better | Same | Comp. Sample III is somewhat better | Comp. Sample III is better |
|---|---|---|---|---|
| 0 | 5 | 13 | 2 | 0 |

As is clear from comparison of Table XXVII and Table XV, the compositions containing cAMP-Na in an amount of 0.1 is greatly effective in preventing graying of the hair and restoring grayed hair to its natural color, although the composition containing the same in an amount of 0.01% has a weak effect.

What is claimed is:

1. A method for restoring grayed human hair to its natural color comprising applying to the scalp for an effective period of time an effective amount of solution comprising:
   (i) a compound selected from the group consisting of compounds of the formula (I)

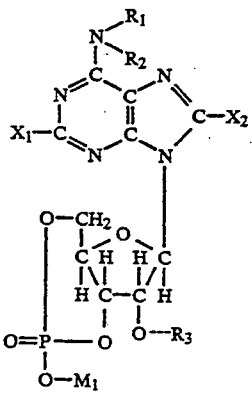

wherein $R_1$, $R_2$ and $R_3$ may be the same or different and each represents a hydrogen atom, an acyl group having 5 to 15 carbon atoms derived from a monocarboxylic acid having 5 to 15 carbon atoms or an acyl group having 2 to 15 carbon atoms derived from a dicarboxylic acid having 2 to 15 carbon atoms or an alkyl group having 1 to 2 carbon atoms; $X_1$ and $X_2$, respectively, represent a hydrogen atom, a halogen, or a mercapto group; with the proviso that when $R_1$, $R_2$ and $R_3$ and $X_1$ are hydrogen atoms at the same time, $X_2$ is not a halogen atom or a mercapto group, and $M_1$ represents a hydrogen atom, an alkali metal or tris(hydroxymethyl)aminomethane, and
   (ii) an inert carrier;
   said compound being present in an amount effective to restore grayed hair to its natural color upon application to the scalp
   provided that the effective amount of compounds wherein every $R_1$, $R_2$ $R_3$, $X_1$ and $X_2$ of the formula is hydrogen is 0.1 to 2 wt % and the effective amount of the compounds wherein at least one of $R_1$, $R_2$, $R_3$, $X_1$ and $X_2$ of the formula is not hydrogen is 0.01 to 2 wt %.

2. The method as set forth in claim 1 wherein the compound represented by the formula (I) is adenosine 3',5'-cyclicphosphoric acid or a salt thereof.

3. The method as set forth in claim 1 wherein the effective amount of the compounds wherein every $R_1$, $R_2$, $R_3$, $X_1$ and $X_2$ of the formula is hydrogen is 0.1 to 2 %.

4. The method as set forth in claim 1 wherein the amount of the compounds wherein at least one of $R_1$, $R_2$, $R_3$, $X_1$ and $X_2$ is not hydrogen is 0.01 to 2 %.

5. The method as set forth in claim 1 comprising applying a hair tonic comprising 0.01 to 2% by weight of said compound of formula (I), 40 to 98% by weight of a lower alcohol, 0 to 15 % by weight of a humectant, 0 to 60% by weight of purified water and a small amount of a perfume.

6. The method as set forth in claim 1 comprising applying a hair cream comprising 0.01 to 2 % by weight of said compound of formula (I), 20 to 80% by weight of an oil, 0.5 to 15 % by weight of a surfactant, 0 to 15 % by weight of a humectant, 15 to 80% by weight of purified water and a small amount of a preservative.

7. The method as set forth in claim 1 comprising applying a milky lotion comprising 0.01 to 2 % by weight of said compound of formula (I), 5 to 30% by weight of an oil, 0.5 to 15 % by weight of a surfactant, 0 to 15 % by weight of a humectant, 50 to 95 % by weight of purified water and a small amount of a preservative.

* * * * *